United States Patent [19]

Fleischer et al.

[11] Patent Number: 5,651,788
[45] Date of Patent: Jul. 29, 1997

[54] MUCOSECTOMY PROCESS AND DEVICE

[75] Inventors: David Elliot Fleischer, Washington, D.C.; Vern L. Liebmann, Reading, Mass.; Steven Lantagne, Salem, N.H.

[73] Assignee: C.R. Bard, Inc., Murray Hill, N.J.

[21] Appl. No.: 443,073

[22] Filed: May 17, 1995

[51] Int. Cl.⁶ .................................................. A61B 17/39
[52] U.S. Cl. .................................................. 606/46; 606/37
[58] Field of Search .................................. 606/10, 11, 12, 606/13, 14, 15, 16, 27, 28, 32, 39, 40, 41, 45, 46, 47, 48, 49, 50

[56] References Cited

U.S. PATENT DOCUMENTS

| | | | |
|---|---|---|---|
| 4,735,194 | 4/1988 | Stiegmann | 128/6 |
| 5,290,284 | 3/1994 | Adair | 606/46 |
| 5,417,697 | 5/1995 | Wilk et al. | 606/46 |

OTHER PUBLICATIONS

Inoue, et al., "Endoscopic mucosal resection with a cap-fitted panendoscope for esophagus, stomach, and colon mucosal lesions," *Gastrointestinal Endoscopy*, 1993, vol. 39, No. 1, pp. 58–62.

Inoue, et al., "Endoscopic resection of early-stage esophageal cancer," *Surgical Endoscopy*, 1991, 5:59–62.

Inoue, et al., "Easy, non-traumatic insertion of a transparent overtube during endoscopic esophagael surgery," *Surgical Endoscopy*, 1991, 5:50.

Inoue, et al., "Endoscopic esophageal mucosal resection using a transparent tube," *Surgical Endoscopy*, 1990, 4:198–201.

Momma, K., et al., "I to Cho (Stomach and Intestine)", 1991, vol. 26, No. 2, p. 198 (Figure) and p. 208 (English summary).

Takemoto, et al., "Significance of Strip Biopsy, with Particular Reference to Endoscopic 'Mucosectomy'," *Digestive Endoscopy*, 1989, vol. 1, No. 1, pp. 4–9.

Primary Examiner—Lee S. Cohen
Assistant Examiner—Sonya Harris-Ogugua
Attorney, Agent, or Firm—Darby & Darby

[57] ABSTRACT

A method of removing abnormal tissue from the gastrointestinal tract of a patient, comprises the steps of introducing an endoscope into the, patient's gastrointestinal tract and applying suction to such abnormal tissue to pull the abnormal tissue into a ligator at the distal end of said endoscope. A ligation band is then applied to the base of the abnormal tissue within the ligator to form a polyp. An electro-surgical snare is then used to sever the polyp from the surrounding tissue.

3 Claims, 1 Drawing Sheet

MUCOSECTOMY PROCESS AND DEVICE

FIELD OF THE INVENTION

This invention relates to mucosectomy procedures. More particularly, this invention relates to an endoscopic procedure which allows for the removal of portions of the mucosa or submucosa from the digestive tract of a human being, and to an instrument for performing such tissue removal.

BACKGROUND OF THE INVENTION

Diagnostic and therapeutic gastrointestinal endoscopy is commonly used to gain access to the digestive tract for the purpose of observing and removing tissue. Common endoscopic therapeutic procedures include cutting, ablating and unclogging through various known mechanisms.

Techniques for obtaining tissues for biopsies include the use of forceps (with or without coagulation), snares or, for cytologic examination, needles and brushes. While these techniques permit the accomplishment of many diagnostic and/or therapeutic goals, in some instances they are inadequate. For example, there currently exists no satisfactory procedure for the removal of flat malignant mucosal lesions or lesions in the submucosa. On some occasions, deep specimens are required for a diagnosis (e.g. lymphoma or Menetrier's disease) in which cases current procedures are limited. Techniques such as "lift and cut" resection and polypectomy after a submucosal injection of a saline or glucose solution have been used but these procedures are not always successful because on some occasions the tissue does not elevate and in others the injection may actually flatten the area making tissue removal more difficult. These procedures, known as endoscopic mucosectomy are becoming increasingly popular, particularly in Japan where early gastric cancer is common.

Early esophageal cancer is an important problem in many parts of the world. With appropriate screening tests, the diagnosis can be made when the disease is limited to the mucosa or even in a premalignant phase. There are known procedures for the destruction of early esophageal cancer (e.g. laser photocoagulation) but there is an existing need for a procedure which will permit the efficient and complete removal of tissue from patients with early esophageal cancer and in the other conditions described above.

It is an object of this invention to provide an improved method for the removal of cancerous and precancerous tissue within the gastrointestinal tract.

SUMMARY OF THE INVENTION

In accordance with the invention, abnormal tissue within the gastrointestinal tract which may be either cancerous or precancerous is identified. The abnormal tissue is then pulled by suction into the distal end of a ligating instrument and banded so as to form a polyp of abnormal tissue. The ligator is then removed from the endoscope and a cutting instrument such as a wire snare introduced through the endoscope and then used to sever the polyp of abnormal tissue from the surrounding healthy tissue.

DESCRIPTION OF THE PREFERRED EMBODIMENT

The invention relates to a mucosectomy procedure which can be applied to any part of the gastrointestinal tract, including the esophagus, the stomach and the small intestine. For purposes of explanation, the invention is described in its preferred embodiment for removal of a mucosal lesion in the esophagus. In practicing the invention, it is contemplated that a conventional ligator and snare may be used although in a preferred embodiment, and as described in detail below, a specially constructed snare is used.

Elastic band ligation is a process used to control bleeding in portions of the gastrointestinal tract. For example, in the treatment of hemorrhoids or esophageal varices, mucosal and submucosal tissue may be entrapped by an elastic ligature Causing strangulation, sloughing off and eventual fibrosis of the lesion. Steigmann U.S. Pat. No. 4,735,194 illustrates a single band ligating instrument which has achieved commercial success as the Steigmann-Goff Clearvue™ single band ligator. The Steigmann patent is hereby incorporated by reference into this specification.

Ligating instruments such as the Steigmann-Goff Clearvue™ ligator are useful in the treatment of esophageal varices and hemorrhoids in which veins that are bleeding or may tend to bleed are isolated by ligation bands; however, ligation has not previously been used for the purpose of treating cancerous and precancerous conditions that may exist in the gastrointestinal tract, in which the abnormal tissue tends to lie flat and is not readily subject to conventional ligation procedures.

Figure 1:
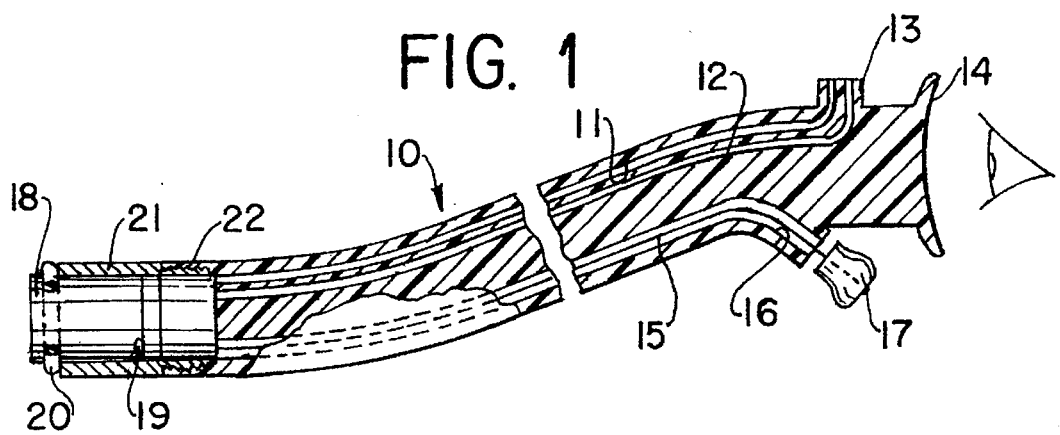
FIG. 1 is a longitudinal view in partial section of the endoscopic ligating instrument in accordance with this invention.

FIG. 1 illustrates a flexible endoscope 10 equipped with a ligator of the type which may be used to practice the invention. Endoscope 10 includes a suction channel 11 and fiberoptics illumination channel 12, both exiting at terminal 13 which is connected to a control box (not shown) for supplying suction and illumination. Eyepiece 14 provides means for viewing the ligation procedure either directly or by video camera and subsequent projection onto a video monitor. Trip wire 15, located in biopsy channel 16, is equipped with weighted handle 17, and is fastened to inner tube 18 at notch 19. Ligating ring 20 is mounted on inner tube 18 at notch 19. Ligating ring 20 is mounted on inner tube 18, which is positioned within outer tube 21. Outer tube 21 is fastened securely to endoscope 10 by means of threaded connection 22.

In utilization of the instrument, elastic ring 20 is mounted over the forward end of the tube 18. Trip wire 15 exiting via biopsy channel 16 is attached to notch 19 at the rearward end of tube 18 and the assembly is placed inside tube 21, which had been securely attached to endoscope 10. Tube 18 is seated within tube 21 with ring 20 protruding just beyond the end of tube 21, as shown in FIG. 1. Trip wire 15 exiting at the rearward end of endoscope 10 is held in tension by weighted handle 17.

After placement of an endoscopic overtube in the patient, the instrument is introduced into the alimentary tract. The target lesion is visualized and the instrument is advanced under direct vision until tube 18 surrounds the intended target. Once full 360° contact is made, suction is activated drawing the lesion into tube 18. When the lesion is totally within tube 18, trip wire 15 is pulled, ring 20 slides off and becomes securely fixed around the base of the target lesion.

Figure 2:
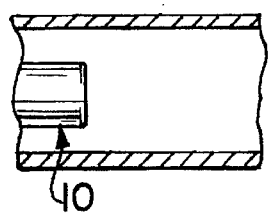
FIGS. 2–8 are schematic representations of a mucosectomy process in accordance with the preferred embodiment of the invention.
Figure 3:
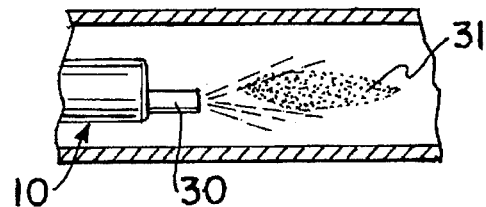
Figure 4:
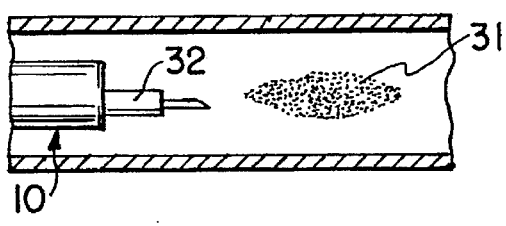
Figure 5:
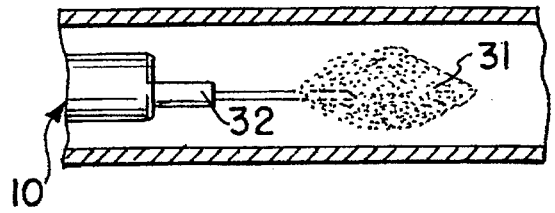

FIGS. 2–8 show how a mucosectomy may be performed in the esophagus in accordance with the invention. Endoscope 10 is introduced into the esophagus at a position adjacent the area to be resected (FIG. 2). After the endoscope is in position, a spray catheter 30 (FIG. 3) is introduced through suction channel 11 and the area in question 31 stained, for example, with Lugol's iodine which is a conventional stain that will turn brown when it contacts tissue cells containing glycogen. Cancerous and precancerous cells do not contain glycogen and therefore do not accept the stain. In this way the abnormal tissue 31 can be identified endoscopically. After the section in question has been stained, the spray catheter 30 is removed and an injection catheter 32 (FIG. 4) introduced through suction channel 11 of the endoscope. A saline solution (for example, 0.9% NaCl) is injected into the stained area to elevate it from the surrounding tissue of the esophagus (FIG. 5). Other material such as glucose solution may be used to elevate the abnormal area.

Figure 6:
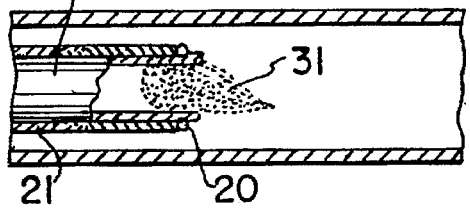
Figure 7:
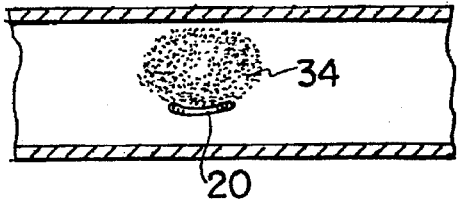

The injection catheter 32 and the endoscope 10 are removed from the patient's esophagus and a single fire ligator is secured to the distal end of the endoscope, as shown in FIG. 1. The endoscope is then reintroduced into the patient's esophagus so that the distal end of the ligator is adjacent the elevated abnormal area (FIG. 6). Suction is applied through suction channel 11 to pull the abnormal area into the ligator. The trip wire 15 is then pulled to apply a ligator band 18 around the base of the abnormal area so that when the ligator is removed, a banded mushroom-like polyp 34 is formed (FIG. 7).

Figure 8:
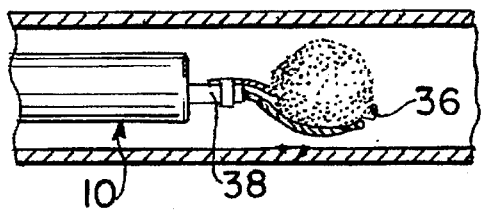

The endoscope 10 is removed from the patient and the ligator detached from the endoscope. The endoscope again is inserted into the esophagus. When the banded "polyp" is in view, a conventional snare comprising a wire loop 36 and sheath 38 may be introduced through the biopsy channel 16 of the endoscope. The snare is positioned so that the wire loop envelops the artificially created polyp (FIG. 8). When the wire loop 36 is pulled into the sheath 38 the polyp is cut from the esophagus and cauterized. The polyp may be withdrawn physically by the snare through the endoscope or released into the patient's gastrointestinal tract.

The snare used in FIG. 8 may be conventional, for example, a monopolar electrosurgery device which simultaneously cuts and cauterizes tissue, such as a polyp or the like. Typically, such snares comprise a wire loop which may be retracted into a sheath causing the loop to tighten around the polyp. The application of voltage simultaneously severs the polyp and cauterizes the wound.

Figure 9:
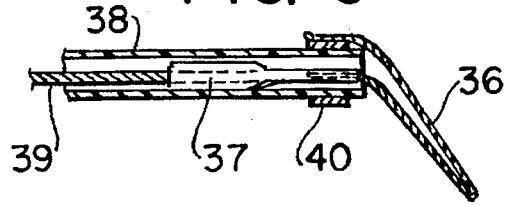
FIG. 9 is a cross-sectional view of the distal end of a snare in accordance with a preferred embodiment of the invention.

The distal end of a snare especially adapted for use with the invention is shown in FIG. 9. The outer sheath of the snare is shown at 38 and the wire loop at 36. A conductive pull wire 39 is attached to the loop 36 by a connector 37 which may be crimped and soldered to adjacent ends of wire 39 and loop 36. Unlike conventional snares, the free end of the wire 36 is connected to a small ferrule 40 which is attached, for example, by adhesive, to the distal end of the sheath 38. The wire loop 36 may be soldered to the ferrule 40. With this arrangement, the loop 36 may be permanently bent at points 42 and 44 so that when the wire 39 is pushed distally (as shown in FIG. 9), the loop which is formed lies in a plane at an angle close to ninety degrees with respect to the longitudinal axis of sheath 38. In contrast to conventional snares in which the loop when extended lies in the same plane as the longitudinal axis of the sheath, the arrangement of FIG. 9 is particularly useful in removing a "polyp" formed by the use of the ligator of FIG. 1 as represented in FIG. 6 and 7. The handle of the snare at its proximal end may be conventional and, therefore, is not illustrated.

Having thus described a preferred embodiment of the present invention, it is to be understood that the above described process and device is merely illustrative of the principles of the present invention, and that other processes and devices may be devised by those skilled in the art without departing from the spirit and scope of the invention as claimed below.

We claim:

1. A method of removing abnormal tissue from surrounding tissue in the gastrointestinal tract of a patient, comprising introducing an endoscope into the patient's gastrointestinal tract;

elevating the abnormal tissue relative to the surrounding tissue by injecting a solution, the abnormal tissue being one of cancerous and precancerous tissue;

applying suction to the elevated abnormal tissue to pull the elevated abnormal tissue into a ligator at the distal end of said endoscope;

applying a ligation band to the base of the abnormal tissue within the ligator to form a polyp consisting of abnormal tissue; and severing said polyp from the surrounding tissue.

2. A method according to claim 1, wherein the abnormal tissue is identified by application of a stain thereto prior to ligation.

3. A method according to claim 1, wherein said polyp is severed by means of an electrosurgical snare which includes an outer sheath and a wire forming a loop which lies in a plane at approximately a right angle to a longitudinal axis of the sheath.

* * * * *